(12) United States Patent
Jahns et al.

(10) Patent No.: US 10,942,159 B2
(45) Date of Patent: Mar. 9, 2021

(54) PRODUCT SUSTAINABILITY SCORECARD

(71) Applicant: Symrise AG, Holzminden (DE)

(72) Inventors: Pasqual Jahns, Höxter (DE); Lena Müller, Münster (DE); Axel Schöning, Holzminden (DE); Helmut Frieden, Höxter (DE)

(73) Assignee: Symrise AG, Holzminden (DE)

( * ) Notice: Subject to any disclaimer, the term of this patent is extended or adjusted under 35 U.S.C. 154(b) by 252 days.

(21) Appl. No.: 16/074,849

(22) PCT Filed: Feb. 4, 2016

(86) PCT No.: PCT/EP2016/052434
§ 371 (c)(1),
(2) Date: Aug. 2, 2018

(87) PCT Pub. No.: WO2017/133779
PCT Pub. Date: Aug. 10, 2017

(65) Prior Publication Data
US 2019/0331655 A1 Oct. 31, 2019

(51) Int. Cl.
*G01N 33/26* (2006.01)
*G06F 17/11* (2006.01)
*C11B 9/00* (2006.01)

(52) U.S. Cl.
CPC ............ *G01N 33/26* (2013.01); *C11B 9/0015* (2013.01); *G06F 17/11* (2013.01)

(58) Field of Classification Search
CPC ......... G01N 33/26; C11B 9/0015; C11B 9/00; G06F 17/11
See application file for complete search history.

(56) References Cited

U.S. PATENT DOCUMENTS

2004/0254742 A1* 12/2004 Long ............... G06Q 10/06
                                                          702/30
2006/0004474 A1    1/2006 Long et al.

OTHER PUBLICATIONS

"Improving Product Sustainability" In: Anonymous: "Colgate Sustainability Report 2013: Giving the World Reasons to Smile", 2013, p. 25, XP002760369.
Schwartz, "Ikea Creates a Sustainability Scorecard for Its Products," Fastcompany.com, Mar. 3, 2011, pp. 1-2, XP002760370.

* cited by examiner

Primary Examiner — Toan M Le
(74) Attorney, Agent, or Firm — Dilworth & Barrese, LLP

(57) ABSTRACT

Suggested is a method for identifying fragrance compounds with low environmental impact and high degree of sustainability encompassing the following steps: (a) providing a fragrance compound or a fragrance composition of interest; (b) calculating scores for each of the following parameters (b1) biodegradability; (b2) biodiversity; (b3) carbon dioxide impact; (b4) process safety with regard to ecological toxicity; (b5) process safety with regard to human toxicity; (b6) land use; (b7) renewability; (b8) traceability; (b9) waste generation; and (b10) water consumption and/or pollution, (c) summing up all scores and calculate the average product sustainability score (PSC); and (d) proceed with those candidates showing a PSC of at least 70.

1 Claim, 10 Drawing Sheets

| Product Tox | Product Eco Tox | E-Factor | Water | Bio Diversity | Land Use | Renewable | Traceability | Bio Degradable | CO2 | Result |
|---|---|---|---|---|---|---|---|---|---|---|
| 80,8 | 86 | 95 | 100 | 100 | 100 | 14,5 | 87,2 | 100 | 58,9 | 82,2 |

| Product Tox | Product Eco Tox | E-Factor | Water | Bio Diversity | Land Use | Renew-able | Traceabi-lity | Bio Degrada-ble | CO2 | Result |
|---|---|---|---|---|---|---|---|---|---|---|
| 80,8 | 86 | 95 | 100 | 100 | 100 | 14,5 | 87,2 | 100 | 58,9 | 82,2 |

Bio Degradable

Bio Diversity

$CO_2$

Process Eco Toxicity

Process Toxicity

Land Use

Renewability

Traceability

Waste

Water

| Fragrance raw material 1 | | Fragrance raw material 2 | | Fragrance raw material 3 | | Fragrance product |
|---|---|---|---|---|---|---|
| Dihydro Myrcenol | + | Dipropylene Glycol | + | Hexyl cinnamic Aldehyde alpha | = | Test Mixture |
| 1238,5 | | 6211,6 | | 1082,2 | | 8532,3 |
| Score: 80,7 | | Score: 79,4 | | Score: 82,0 | | Score: 82,2 |

Figure 6

PRODUCT SUSTAINABILITY SCORECARD

FIELD OF INVENTION

The present invention belongs to the area of cosmetics in general and fragrances in particular and refers to a method for identifying the environmental impact of new compounds with regard to key parameters as for example biodegradability and carbon dioxide production.

STATE OF THE ART

Worldwide companies develop, produce and sell about hundred thousand fragrances, flavours and cosmetic ingredients which are based on roughly 50,000 mostly natural raw materials, as for example vanilla, citrus products, onions, fish, meat or flower and plant materials.

With extensive global sourcing comes great responsibility. According to regulatory requirements with increasing complexity every year new products are subject to strict sustainability requirements. Moving towards a sustainable product development, it is desirous to anticipate coming legal requirements by rating the chemical substances sourced in particular for fragrances individually, to get a better understanding of the degree of sustainability for each product. The aim of the present invention is providing a scoring model, called "Product Sustainability Scorecard" to increase transparency of the environmental impact of fragrances and related raw materials to facilitate product development. Therefore, the aim of the present invention is providing a method to satisfy the needs explained above.

SUMMARY OF THE INVENTION

Object of the present invention is a method for identifying fragrance compounds with low environmental impact and high degree of sustainability encompassing the following steps:
(a) providing a fragrance compound or a fragrance composition of interest;
(b) calculating scores for each of the following parameters
    (b1) biodegradability;
    (b2) biodiversity;
    (b3) carbon dioxide impact;
    (b4) process safety with regard to ecological toxicity;
    (b5) process safety with regard to human toxicity;
    (b6) land use;
    (b7) renewability;
    (b8) traceability;
    (b9) waste generation; and
    (b10) water consumption and/or pollution,
(c) summing up all scores and calculate the average product sustainability score (PSC); and
(d) proceed with those candidates showing a PSC of at least 70.

The Product Sustainability Scorecard ("PSS") allows measuring the material performance within the following parameters which are considered having the highest impact on environment as compiled in parameters (b1) to (b10).

The results from PSS allow evaluating the environmental impact of fragrance prior to its production based on fundamental research results. In order to provide new compounds which not only match with market requirements in terms of olfactory performance, but also comply with regulatory requirements and the overall approach for providing only new products with high sustainability and low environmental impact, the invention is not a simple instruction to human mind, but provides a technical teaching which shortens development times and is therefore also of serious economic importance.

BRIEF DESCRIPTION OF THE DRAWINGS

The present invention will be described in greater detail with reference to the accompanying drawings, in which:

FIG. 2a shows a table presenting the consolidated results of a typical product scoring;

FIG. 2b illustrates a radar diagram of the results as shown in FIG. 2a;

FIG. 6 schematically illustrates the recipe/fragrance formula consisting of 44DHM, DPG and HCA.

DESCRIPTION OF THE INVENTION

Figure 1:
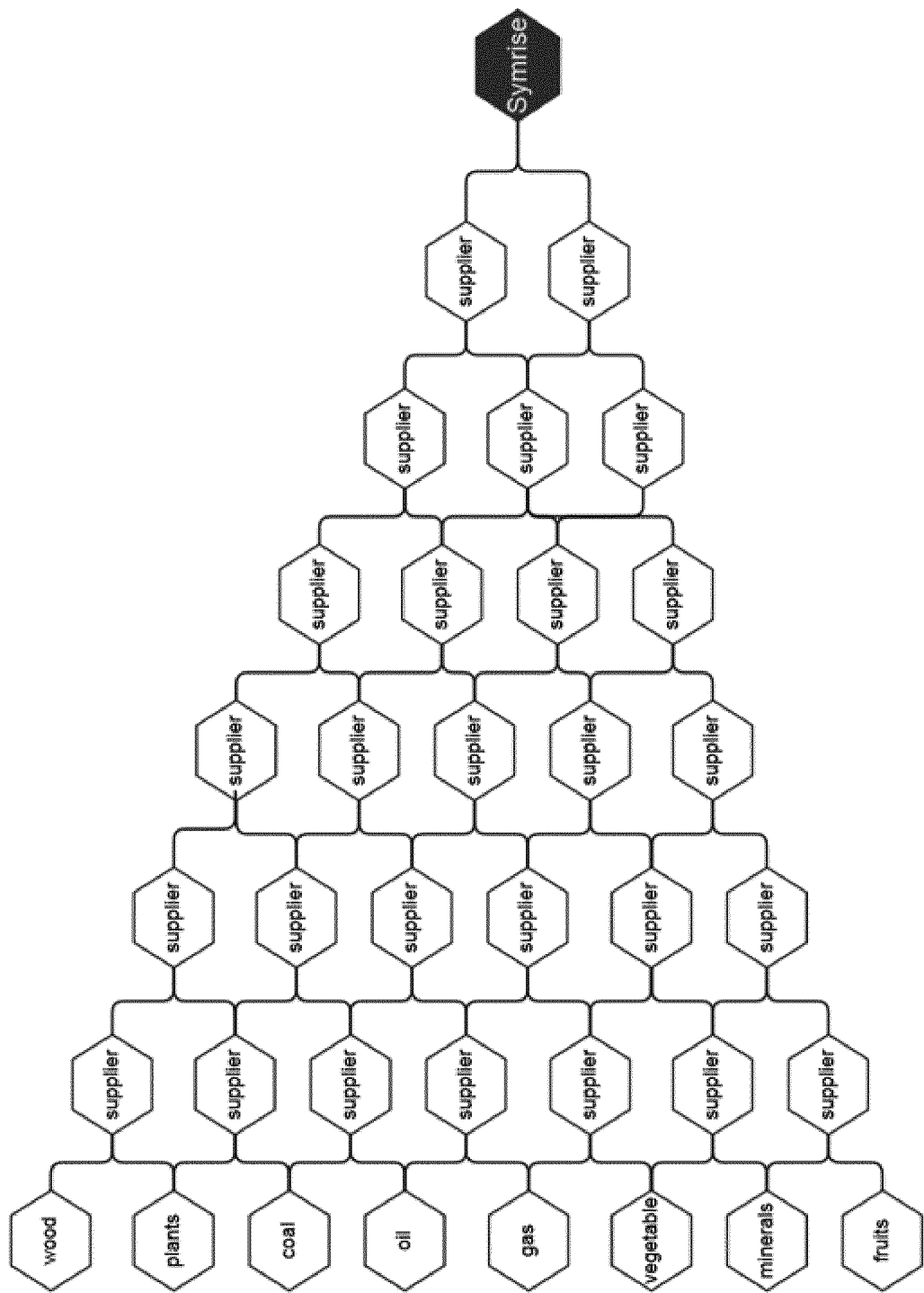
FIG. 1 schematically illustrates an overview of the entire value chain from basic chemicals to raw materials suitable for fragrance production.

All parameters of the model are normalized to a scale from 0 to 100 without a dimension. However, units of pre-calculation steps are defined in the aspects of the different scorecard parameters. Objects of investigation for the scorecard were minimum 80% of the top raw materials, extrapolated to the entire material portfolio.

Environmental aspects of raw materials from waste streams like e.g. an orange peel, eucalyptus leafs etc. are not considered in this model.

Valuable side streams such as dipropylene glycol from 1,2-Propandiol production are allocated according to their molar masses. For example calculation for carbon dioxide impact followed the equation:

(Propylene oxide $CO_2$ value*Propylene oxide Molar Mass+Propylene glycol $CO_2$ value*Propylene glycol Molar Mass)/Dipropylene glycol Molar Mass System Boundaries Table 1 provides an overview of factors possibly occurring in the life cycle of cosmetic products in general and fragrances in particular, but were not considered in the course of the present invention:

TABLE 1

| | System boundaries |
|---|---|
| Factor | Background |
| Transport | Transport is considered to have minor impacts in comparison to processing of raw materials. |
| Services | Services are considered to have minor impacts in comparison to processing of raw materials. |

TABLE 1-continued

System boundaries

| Factor | Background |
| --- | --- |
| Catalysts | The use of catalysts is often non-public information. However, catalysts are usually only used in low dosages and can be reused several times before disposal. The environmental impact is therefore considered as low. |
| Solvents used | The use of solvents is often non-public information. However, solvents are usually cleaned after usage and reused several times before disposal. The standard factors for distillation/crystallization also include distillation of solvents. Due to strong customer requirements, critical solvents like ICH Q3c class 1 and 2 are usually strictly controlled. After reviewing related supplier information, only ten raw materials identified came from suppliers who stated that class 1 or 2 solvents could be included. Reviewing five possible solvents, we found out that they seem to be caused mainly by precursors e.g. Toluene, Methanol or Benzene as reactants. This aspect is already assessed by the (Eco) Toxicity evaluation. For the other five materials, only class 2 materials are used and volume use in fragrances is low. For these reasons QC specifications are sufficient to restrict the critical use of such solvents. |
| Carbon footprint related data | Heating or cooling is not evaluated due to low impact (low specific heat capacity in comparison to distillation or crystallization) e.g. warming of acetic acid to 800° C. produces a carbon footprint of approx. 0.1 kg $CO_2$/kg product<br>Energy consumption like e.g. pumping, warming of raw material, heating of buildings of administration etc. is not considered due to low relevance<br>Packaging is excluded. High volume products are usually delivered in reusable containers and the impact is comparably low.<br>Other GHG emissions such as $CH_4$ and $N_2O$ are not considered due to low relevance. The $CO_2$ factor is seen as sufficient to evaluate possible impact.<br>$CO_2$ related to deforestation is not considered. Land use parameters are used instead.<br>The individual energy mix is only considered if known, otherwise standard factors are used. |
| Volatile Organic Compound | VOCs are not considered. Most of the ingredients of fragrances fall into this category, making comparisons redundant. |
| Equipment used | The environmental footprint of equipment is not considered. Usually equipment is used for long periods and the impact is negligible. |
| Genetic Modified Organism | GMOs may have an impact to e.g. biodiversity, but the direct use of such materials is low and derivatives from global markets are mostly commodities and possible influences to agriculture practices is also low. In the scope of the top 80% raw materials no GMO is identified. |
| Convention on International Trade in Endangered Species of Wild Fauna and Flora (CITES) Materials | As far as some of these materials are still being used, certifications are provided. CITES materials are not in the scope of the top 80% fragrance portfolio. |
| Animal derived materials | Very low volumes of animal derived materials are used in fragrances. Therefore materiality is considered as quite low. |

Selection of Scorecard Criteria

One essential step of sustainable business is to make business related issues transparent to the public. Traceability thorough the entire supply chain is a crucial parameter. It is therefore an important aspect defined in the present product sustainability scorecard. Another guide to the present invention represent the so-called "nine planetary boundaries", a central concept in an earth system framework proposed by a group of earth system and environmental scientists. The framework was first introduced in 2009, when a group of 28 internationally renowned scientists identified and quantified the first set of nine planetary boundaries within which humanity can continue to develop and thrive for generations to come. Crossing these boundaries could generate abrupt or irreversible environmental changes. Respecting the boundaries reduces the risks to human society of crossing these thresholds. It is one scope of the present invention to assess related concerns. The planetary boundaries are shown in Table 2:

TABLE 2

Planetary boundaries

| Planetary Boundaries | Main causes |
| --- | --- |
| 1. Stratospheric ozone depletion | Anthropogenic ozone-depleting chemical substances |
| 2. Loss of biosphere integrity (biodiversity loss and extinctions) | Demand for food, water and natural resources |
| 3. Chemical pollution and the release of novel entities | Emissions of Toxicity and long-living substances such as synthetic organic pollutants, heavy metal compounds and radioactive materials |
| 4. Climate Change | $CO_2$ |
| 5. Ocean acidification | $CO_2$ |
| 6. Freshwater consumption and the global hydrological cycle | Water use, $CO_2$ |

TABLE 2-continued

Planetary boundaries

| Planetary Boundaries | Main causes |
|---|---|
| 7. Land system change | Forests, grasslands, wetlands and other vegetation types have primarily been converted to agricultural land |
| 8. Nitrogen and phosphorus flows into the biosphere and oceans | Fertilizer production and application |
| 9. Atmospheric aerosol loading | Many pollutant gases condense into droplets and particles, also through land use change which increases the release of dust and smoke into the air |

Another guide to the present invention are the so-called "12 principles of Green Chemistry", which also define environmental impact of a compound Green chemistry is an area of chemistry and chemical engineering focused on the design of products and processes that minimize the use and generation of hazardous substances. Paul Anastas of the U.S. Environmental Protection Agency formulated some simple rules of thumb for how sustainability can be achieved in the production of chemicals—the "Green chemical principles". The principles are summarised in Table 3:

TABLE 3

Principles of Green Chemistry
Green Chemistry Principle

1. PREVENTION
It is better to prevent waste than to treat or clean up waste after it has already been created.
2. ATOM ECONOMY
Synthetic methods should be designed to maximize the incorporation of all materials used in the process for the final product.
3. LESS HAZARDOUS CHEMICAL SYNTHESES
Wherever possible, practicable synthetic methods should be designed to use and generate substances that possess little or no toxicity to human health and the environment.
4. DESIGNING SAFER CHEMICALS
Chemical products should be designed to affect their desired function while minimizing their toxicity.
5. SAFER SOLVENTS AND AUXILIARIES
The use of auxiliary substances (e.g., solvents, separation agents, etc.) should be made unnecessary wherever possible and innocuous when used.
6. DESIGNING FOR ENERGY EFFICIENCY
Energy requirements of chemical processes should be recognized for their environmental and economic impacts and should be minimized. If possible, synthetic methods should be conducted at ambient temperature and pressure.
7. USE OF RENEWABLE FEEDSTOCKS
A raw material or feedstock should be renewable rather than depleting whenever technically and economically practicable.
8. REDUCE DERIVATES
Unnecessary derivatization (use of blocking groups, protection/deprotection, temporary modification of physical/chemical processes) should be minimized or avoided if possible, because such steps require additional reagents and can generate waste.
9. CATALYSIS
Catalytic reagents (as selective as possible) are superior to stoichiometric reagents.
10. DESIGN FOR DEGRADATION
Chemical products should be designed so that at the end of their function they break down into innocuous degradation products and do not persist in the environment.
11. REAL-TIME ANALYIS FOR POLLUTION PREVENTION
Analytical methodologies need to be further developed to allow for real-time, in-process monitoring and control prior to the formation of hazardous substances.
12. INHERENT SAFER CHEMISTRY FOR ACCIDENT PREVENTION
Substances and the form of a substance used in a chemical process should be chosen to minimize the potential for chemical accidents, including releases, explosions, and fires.

Considering traceability of products the nine planetary boundaries and twelve principles of green chemistry formed a basis for calculating possible impact of products on environment in terms of the ten categories presented above. From these findings ten criteria for setting up a Product Sustainability Scorecard were developed.

Basically, all fragrance compositions can be covered by the methodology according to the present invention. A minimum of 80% of raw material by mass (kg) is evaluated.

The Method of Scoring and Weighting of Scorecard Criteria

FIG. 1 provides an overview of the entire value chain from basic chemicals to taw materials suitable for fragrance production.

The following parameters were identified as important to meet the requirements for sustainable product development.
Biodegradability,
Biodiversity,
$CO_2$ production,
(Eco-) Toxicity,
Land use,
Renewability,
Traceability,
Waste production and
Water consumption.

All parameters were considered to be of equal importance. The result of all parameters can be averaged to score a singly raw material or a complete formula. In the following it is explained in detail how the scores for each of the parameters (b1) to (MO) can be calculated.

Biodegradability

Biodegradation is one of the most important factors in assessing the environmental fate of chemicals. Biodegradation is the chemical dissolution of materials by bacteria, fungi, or other biological means. Biodegradability is evaluated according to the OECD Method 301/302 or equivalent. The tests of the OECD test series 301 (A-F) verify whether a substance is able for complete biodegradation under aerobic conditions. Different test methods are available for well or poorly soluble as well as volatile substances. The test usually takes 28 days. Test items must reach 60% biodegradation within 10 days to be classified as 'ready biodegradable'.

The scoring of precursors of petro-chemicals has no influence on the scoring of the product. It is assumed that such precursors are used in the production process, making them irrelevant for the assessment of the final product.

For products made of renewable material with high E-factors and low biodegradability in low regulated countries, it is assumed that residues in waste could harm the environment. Therefore the values of biodegradability of precursors are also taken into account for the product scorecard (e.g. peppermint oil).

The scoring is illustrated by the following Scheme 1:

Scheme 1: Scoring

STEP 1 Evaluation of the "Biodegradability Score" of the fragrance raw material based on the following scoring system

| . . . | "Ready Biodegradable" according to OECD 301 | >The scoring is based on the biodegradation value of a chemical according to OECD 301; e.g. 70% biodegradation after 28-day test period = score of 70 | Data Source: 'Ready Biodegradable' Certificate |
|---|---|---|---|
| 000 | No data available | >If no data is available, a score of 0 applies | Data Source: / |

Biodiversity

Biodiversity is the variety of different types of life found on earth and the variations within species. Possible impacts to Biodiversity are evaluated as compiled in Table 3:

TABLE 3

Typical impacts on biodiversity

| Typical Impacts | |
|---|---|
| Habitat Removal and Alteration | Conversion of lands to agriculture and/or poor agricultural practices (e.g. crop rotation, fertilizer, pesticides) also degrade soil quality and reduce species. |
| Land use | Covered in Land use parameter. |
| Overharvesting/Overexploitation | Usually applicable to wood products and considered accordantly. |
| Pollution (Water/Air) | Covered in (Eco) Toxicity parameter |
| Introduction of exotic species | Usually not applicable due to low relevance of animal derivatives in fragrances. However, if issues are known related to Symrise raw material this aspect will be evaluated too. |
| Climate change | Covered in $CO_2$ parameter |
| Genetic modified organism (GMO) | GMOs may have an impact to e.g. biodiversity, but the direct use of such materials is low and derivatives from global markets are mostly commodities were possible influences to agriculture practices is also low. |
| Water use | High impact on biodiversity losses related to water stress (see https://www.cbd.int/iyb/doc/prints/iyb-netherlands-watercrisis.pdf). Covered in water parameter. |
| Using raw material from endangered species | The approach of Symrise is to avoid such materials. However, some of these materials are still being used, but only if certifications are provided. |

The scoring is illustrated by the following Scheme 2:

Scheme 2: Scoring

STEP 1 Evaluation of the "Bio-Diversity Score" of the fragrance raw material based on the following scoring system

| 100 | Reactant is side product/results from waste streams | >If a substance is a side product from a resource (e.g. orange, wood) that was cultivated for other purposes in the first place, a score of 100 applies. Primary products, such as orange juice or wood for the furniture industry may harm the environment. However, users of so called "waste products" (such as orange peels) have a low impact, as the environment would also be harmed without using waste streams. | Data Source: Research |

| | | |
|---|---|---|
| 100 Reactant results from chemical synthesis (without known issues) | >If a substance results from chemical synthesis, the impact of process pollutions and climate change are already covered and therefore a score of 100 applies. | Data Source: Research |
| 100 Naturals from non-biodiversity hotspots | >If naturals are sourced from biodiversity hot spots the risk of destruction of biodiversity by traditional farming is high. Sourcing of material from non-critical areas is considered as not highly risky. To identify possible biodiversity hotspots where highest risks to biodiversity are expected, the following tool was used: http://www.cepf.net/resources/hotspots/Pages/default.aspx | Data Source: Research/Link |
| 100 Global bulk products → Production volume of >1.000 t/annum | >For big bulk products which are produced in more than 1.000 t/annum a score of 100 applies since products derived in high tonnages are considered as less critical. A detailed list can be found here: Basic Chemicals and Production and here http://echa.europa.eu/de/ 1000 t is the threshold value of REACH. Experience has shown that large producers have a high degree of automatization ensuring advanced process control due to REACH requirements and cost pressure. Small suppliers are not as well-positioned. | Data Source: List of Basic Chemicals and Production Volumes / http://echa.europa.eu/de/ |
| 100 Naturals UEBT verified | >UEBT is one of the highest global certification standards for biodiversity | Data Source: Certification |
| 075 Naturals UEBT member and raw material self-assessment (Rating > 75%) | >If naturals are not UEBT verified but at least UEBT member, a score of 75 applies, since UEBT members are regularly audited | Data Source: Certification |
| 075 Naturals Global GAP, Rainforest Alliance, Fair Trade, RSPO etc. | >If naturals are verified by GAP, Rainforest Alliance, Fair Trade or RSPO, a score of 75 applies. Such certification usually limits fertilizers and pesticides. Also some additional environmental measures are enforced. | Data Source: Certification |
| 050 Origin from EU countries | >The EU has started to link subsidies related to good environmental practice | Data Source: Sourcing Information |
| 025 Own growing standard including biodiversity topics not externally verified | >Some supplier set own standards to e.g. limit the use of fertilizers and pesticides | Data Source: Certification |
| 000 Naturals, No further information | >If no data is available, a score of 0 applies | Data Source: / |

STEP 2 Calculation of the "Biodiversity Score" (BS) of the fragrance raw material. Each reactant counts into the product result related to molar masses used:

$$BS = \frac{\left(\begin{array}{l}'\text{Reactant } A \text{ Molar Mass}' * '\text{Reactant } A \text{ Biodivers.}' + \\ '\text{Reactant } B \text{ Molar Mass}' * '\text{Reactant } B \text{ Biodivers.}'\end{array}\right)}{('\text{Reactant } A \text{ Molar Mass}' + '\text{Reactant } B \text{ Molar Mass}' + \ldots)}$$

Carbon Dioxide Impact

Carbon dioxide emissions are those stemming from the burning of fossil fuels and the manufacturing of cement. They include carbon dioxide produced during consumption of solid, liquid, and gas fuels and gas flaring. The scoring is illustrated by the following Scheme 3:

Scheme 3: Scoring

STEP 1 Research of the $CO_2$ emissions of each reactant based on public databases like Probas.

STEP 2 Calculation of the $CO_2$ emissions of the fragrance raw material resulting from its reactants ("Reactant Based $CO_2$ Emissions"=RBCE). Each reactant counts into the product result related to molar masses used:

$$RBCE = \frac{\left(\begin{array}{l}'\text{Reactant } A \text{ Molar Mass}' * '\text{Reactant } A \text{ CO}_2' + \\ '\text{Reactant } B \text{ Molar Mass}' * '\text{Reactant } B \text{ CO}_2 \ldots '\end{array}\right)}{'\text{Product Molar Mass}'}$$

STEP 3 Addition of $CO_2$ emissions resulting from processing:

Reactant based $CO_2$ emissions+Process based $CO_2$ emissions

The following 'standard processing factors' are used (Table 4). These standard factors are based on average indicators of the industry and internal assumptions. If further information is available such data will be used preferably.

TABLE 4

Standard processing factors

| Process | Distillation | Pyrolysis | Pyrolysis & Distillation | Distillation & Crystallization | Crystallization | Fermentation & Crystallization | Water Steam Distillation (generic) | Blending | No Processing | Cracking |
|---|---|---|---|---|---|---|---|---|---|---|
| Kg $CO_2$/Kg Product | 1 | 1 | 2 | 2 | 1 | 1 | n.a. | 0 | 0 | n.a. |
| Losses | 10% | 10% | 20% | 20% | 10% | 10% | 0% | 0% | 0% | 26.8 |

STEP 4 Addition of $CO_2$ emissions related to process losses:
If no actual data is available, losses are calculated very conservatively with 10% of each intensive processing step. Losses are generally understood as the additional percentage of material needed to gain 100% of the product: e.g. for one composed molecule 1.1 times of the reactants and process energy is needed (+10%). Calculate Overall Cos emissions (OCE) according to following equation:

$$OCE = (\text{'Product based } CO_2 \text{ emissions'} + \text{'Process based } CO_2 \text{ emissions'}) * (1 + \text{'\% Losses'})$$

STEP 5 Normalization to scale 0 to 100 (Negative result is set to 0):

$$CO_2 \text{ Score} = (10 - \text{Overall } CO_2 \text{ Emissions}) * 10$$

The normalization with 10 kg $CO_2$ per Kg product as upper limit for differentiation (everything above scores 0 as well), covers the vast majority of products in the portfolio and follows internal expert judgment.

Process Safety (Eco Toxicity and Toxicity)

Hazard statements form part of the 'Globally Harmonized System of Classification and Labelling of Chemicals' (GHS). They are intended to form a set of standardized phrases about the hazards of chemical substances and mixtures.

H200: Physical Hazards (=Toxicity and Eco Toxicity)
H300: Health Hazards (=Toxicity)
H400: Environmental Hazards (=Eco Toxicity)

The scoring is illustrated by the following Schemes 4 and 5:

Scheme 4 and 5: Scoring

STEP 1 Evaluation of the '(Eco) Toxicity Material Score' and 'Critical By-Product Score' of each reactant and its potential by-products based on the safety according to material properties:

| | H-Phrases (Eco) Toxicity | >In each step of the value chain H-Phrases of raw materials are scored according to their criticality. The worst result is used for evaluation. Definitions and scorings of each H-Phrase can be found here: H-Phrases Eco Toxicity | Data Source: List of H-Phrases (Eco) Toxicity (see Appendix) |
|---|---|---|---|

STEP 2 Evaluation of the '(Eco) Tox Supplier Score' of each reactant based on process safety according to chemical handling (see appendix for further information):

| | | Country of origin | | >Countries with a strong Regulatory Quality and strong Rule of Law get higher ratings than countries with lower ratings due to their lower inherent risk. Further descriptions can be found here: World Bank | Data Source: List of World Bank Country Ratings (see Appendix) |
|---|---|---|---|---|---|
| | 100 | Global bulk products → Production volume of >1.000 t/annum | | >For big bulk products which are produced in more than 1.000 t/annum a score of 100 applies since products derived in high tonnages are considered as less critical. A detailed list can be found here: Basic Chemicals and Production and here http://echa.europa.eu/de/ 1000 t is the threshold value of REACH. Experience has shown that large producers have a high degree of automatization ensuring advanced process control due to REACH requirements and cost pressure. Small suppliers are not as well-positioned. | Data Source: List of Basic Chemicals and Production Volumes (see Appendix) / http://echa.europa.eu/de/ |
| | 100 | Certification/ Assessment | SMETA/ISO 14001 audited successfully | >If SMETA/ISO 14001 is audited successfully, a score of 100 applies. | Data Source: Certification |
| | 075 | | SEDEX SAQ assessment (low risk) | >If SEDEX SAQ assessment result is 'low risk', a score of 75 applies. | Data Source: Certification |

-continued

| | | | |
|---|---|---|---|
| 050 | SEDEX SAQ assessment (medium risk) | >If SEDEX SAQ assessment result is 'medium risk', a score of 50 applies. | Data Source: Certification |
| 000 | SEDEX SAQ assessment (high risk) | >If SEDEX SAQ assessment result is 'high risk', a score of 0 applies. | Data Source: Certification |

STEP 3 Calculation of the overall '(Eco) Tox Score' of each reactant and the final product. Distinction is to be made between these two cases:
(i) Base materials: For a base materials, the material score and supplier score are compared. If the supplier score is better, it outweighs the material score—following the assumption that a safe and controlled production environment is able to avert the risks of hazardous materials:

MAX('(Eco) Tox Material Score';'(Eco) Tox Supplier Score')=(Eco) Tox Score (ii) Composed products: For composed products the (Eco) Tox Score combines the hazard and supplier information of the composed product itself (calculated as above) with the (Eco) Tox Score of its reactants. The latter accounts for one third of the overall Tox Score:

⅔*MAX('(Eco) Tox Material Score';'(Eco) Tox Supplier Score')+⅓*'backpack of reactants'=(Eco) Tox Score The backpacks of the reactants are the average of their own (Eco) Tox Scores weighted (by molar mass):

$$\text{'backpack of reactants'} = \frac{\begin{pmatrix} \text{'React. A (Eco) Tox Score'} * \text{'React. A Mol. Mass'} + \\ \text{'React. B (Eco) Tox Score'} * \text{'React. B Mol. Mass'} \end{pmatrix}}{(\text{'Reactant A Molar Mass'} + \text{'Reactant B Molar Mass'})}$$

The hazard and supplier information of the product counting for ⅔ of the overall score puts an emphasize on the process steps closer to Symrise (and its management access)

STEP 4 In addition to the '(Eco) Tox Score' the '(Eco) Tox Process Score' is calculated. This score (only taking the last process step into account) compares the hazard risk of the product with the one of the potential by-products. The lowest (worst) score takes the lead:

MIN('(Eco) Tox Material Score';'Critical By-Product Score')=(Eco) Tox Process Score Example: If a product has an '(Eco) Tox Material Score' of 75 but its by-product has a score of 25, 25 is used.

Handling of Data Gaps

Usually big petro-chemical bulk commodities are available on the world market. Due to the highly optimized processes and experience with such suppliers it is assumed that such materials are managed in a safe manor and therefore Supplier Score Social and Supplier Score Environmental will be set to a maximum of 100. A list of related materials can be found here: http://echa.europa.eu/de/information-on-chemicals If no further certification of environmental performance of supplier is available, a general country rating provided by the World Bank is used to create risk factors related to material handling. Countries with a strong Government Effectiveness/Regulatory Quality and strong Rule of Law receive higher ratings than countries with lower ratings due to their lower inherent risk.

Land Use

Land use for cultivation and production units results in a loss of biodiversity. Also discharges of toxic substances in soil and water cause damage to ecosystems. The scoring is illustrated by the following Scheme: 6

Scheme 6: Scoring

STEP 1 Evaluation of the 'Land use Score' of each reactant based on the following scoring system:

| | | |
|---|---|---|
| 100 | Reactant is side product/ results from waste streams | >If a substance is a side product from a resource (e.g. orange, wood) that is cultivated for other purposes in the first place, a score of 100 applies. Primary products, such as orange juice or wood for the furniture industry may harm the environment. However, users of so called "waste products" (such as orange peels or eucalyptus leafs) have a low impact since the environment would also be harmed without using waste streams. |
| 100 | Reactant results from chemicals synthesis (without known issues) | >If a substance results from chemical synthesis, a score of 100 applies. Land used for chemical plants or oil rigs are low compared to agriculture. |
| 075 | Acreage of 10 t/ha = 75 | >e.g. Potatoes. Source: http://www.agrarheute.com/kartoffelernte-2014-mars |
| 050 | Acreage of 1 t/ha && <=10 t/ha = 50 | >e.g. Palm Oi Source: http://www.palmoilworld.org/about_malaysian-industry.html |
| 025 | Acreage of >100 kg/ha & <=1 t/ha = 25 | >e.g. Peppermint. Source: http://www.downtoearth.org.in/news/farmers-quit-mentha-32914 |
| 000 | Acreage of <100 kg/ha = 0 | >e.g. Vetiver Source: http://www.sugandhim.com/images/f&f_industry_articles/vetiver_oil_%28Khus%29.pdf |
| 000 | No data available | >If no data is available, a score of 0 applies |

STEP 2 Calculation of the 'Land use Score' of composed products. Each reactant counts into the product with the weight of its molar mass:

$$\frac{\begin{pmatrix} 'React.\ A\ Molar\ Mass' * 'React.\ A\ Land\ use' + \\ 'React.\ B\ Molar\ Mass' * 'React.\ B\ Land\ use\ \ldots\ ' \end{pmatrix}}{('Reactant\ A\ Molar\ Mass' + 'Reactant\ B\ Molar\ Mass')} = \text{Land use Score}$$

Renewability

Renewability means the use of renewable resources for environmental protection. The scoring is illustrated by the following Scheme 7.

Scheme 6: Scoring

STEP 1 Evaluation of the 'Renewability Score' of each reactant based on the following scoring system:

| | | | |
|---|---|---|---|
| 100 | Reactant is renewable | >If a resource is renewable, a score of 100 applies. | Data Source: Research |
| 000 | Reactant is not renewable | >If a resource is not renewable, a score of 0 applies. | Data Source: Research |

STEP 2 Calculation of the 'Renewability Score' of composed products. The calculation is based on the number of C-atoms:

Example SANDRANOL (only the renewable C-atoms are labelled)

10 of 14 C-atoms (71.43%) in the molecule come from renewable sources 4 Renewability Score=71.43:

Case 1: The number of C-Atoms of the product equals the sum of the C-Atoms of the reactants:

$$\frac{\begin{pmatrix} 'React.\ A\ C\text{-Atoms}' * 'React.\ A\ Renewab.\ Score' + \\ 'React.\ B\ C\text{-Atoms}' * 'React.\ B\ Renewab.\ Score' \end{pmatrix}}{'Product\ C\text{-Atoms}'} = \text{Renewability Score}$$

Case 2: The product has less C-Atoms than the reactants (C-Atoms going into waste or by-product): Expert judgement is needed to allocate the renewable and nonrenewable C-Atoms to product and waste/by-product.

Traceability

Supply Chain transparency and disclosure are essential for the improvement of sustainability throughout the whole value chain. The scoring is illustrated by the following Scheme 8.

Scheme 8: Scoring

STEP 1 Evaluation of the 'Traceability Score' of each reactant based on the following scoring system:

| | | | |
|---|---|---|---|
| 100 | Reactant results from chemicals synthesis (without known issues) | >If a substance results from chemical synthesis, a score of 100 applies. It is assumed that chemical companies are able to trace back raw materials by unique identifiers or defined time frames due to their high grade of automation. | Data Source: Research |
| 100 | Global bulk products → Production volume of >1.000 t/annum | >For big bulk products which are produced in more than 1.000 t/annum a score of 100 applies since products derived in high tonnages are considered as less critical. A detailed list can be found here: Basic Chemicals and Production and here http://echa.europa.eu/de/ 1000 t is the threshold value of REACH. Experience has shown that large producers have a high degree of automatization ensuring advanced process control due to REACH requirements and cost pressure. Small suppliers are not as well-positioned. | Data Source: List of Basic Chemicals and Production Volumes (Appendix) / http://echa.europa.eu/de/ |
| 100 | Traceable up to the field | >If a reactant is traceable up to the field, it is considered the highest level of traceability and therefore scored with 100. | Data Source: Research |
| 075 | Grower known | >If the grower is known, a score of 75 applies. | Data Source: Research |
| 050 | Region of country of origin known | >If the region within the country of origin is known, a score of 50 applies. | Data Source: Research |
| 025 | Country of origin known | >If the country of origin is known, a score of 25 applies. | Data Source: Research |
| 000 | Only trader known | >If only the trader is known, no transparency is assured. | Data Source: Research |
| 000 | No data available | >If no data is available, a score of 0 applies | Data Source: / |

STEP 2 Calculation of the 'Traceability Score' of composed products. Each reactant counts into the product result related to molar masses:

$$\frac{\begin{pmatrix} 'React.\ A\ \text{Molar Mass}' * 'React.\ A\ \text{Traceability}' + \\ 'React.\ B\ \text{Molar Mass}' * 'React.\ B\ \text{Traceability}\ ...\ ' \end{pmatrix}}{('\text{Reactant}\ A\ \text{Molar Mass}' * '\text{Reactant}\ B\ \text{Molar Mass}')} = \text{Traceability Score}$$

Generation of Waste—E-Factor

To assess waste generated by synthesis, the so-called E-factor (environmental factor) is used. It is calculated using this formula: E-factor=kg waste/kg reactants. The scoring is illustrated by the following Scheme 9.

Scheme 9: Scoring

STEP 1 Research of the E-factor of each basic material in public databases like Probas STEP 2 Calculation of the E-factor of the reactants of composed products. Each reactant counts into the product result related to molar masses:

$$\frac{\begin{pmatrix} '\text{Reactant}\ A\ \text{Molar Mass}' * '\text{Reactant}\ A\ E\text{-Factor}' + \\ '\text{Reactant}\ B\ \text{Molar Mass}' * '\text{Reactant}\ B\ E\text{-Factor}\ ...\ ' \end{pmatrix}}{'\text{Product Molar Mass}'} = \text{Reactant based}\ E\text{-Factor}$$

STEP 3 Calculation of the E-factor due to unused atoms:

$$\frac{\begin{pmatrix} '\text{Reactant}\ A\ \text{Molar Mass}' + '\text{Reactant}\ B\ \text{Molar Mass}\ ...\ ' - \\ '\text{Product Molar Mass}' \end{pmatrix}}{'\text{Product Molar Mass}'} = \text{unused atoms}$$

STEP 4 Calculation of the overall E-factor including losses: Losses are handled identically to the $CO_2$ calculation. In contrast to unused atoms losses do not relate to waste by design (by-products etc.) but to waste due to losses of the product itself. For further information see section 3 ($CO_2$)

(Reactant based $E$-Factor+unused Atoms)*(1+Losses)=Overall $E$-Factor

STEP 5 Normalization to scale 0 to 100 (Negative result is set to 0):

(10−Overall $E$-Factor)*10=Waste/$E$-Factor Score

The normalization with 10 kg waste per kg product as upper limit for differentiation (everything above scores 0 as well) covers the vast majority of products in the portfolio and follows internal expert judgment.

Exceptions

| | | | |
|---|---|---|---|
| 100 | Reactant is side product/ results from waste streams | >If a substance is a side product from a resource (e.g. orange, wood) that is cultivated for other purposes in the first place, a score of 100 applies. Primary products, such as orange juice or wood for the furniture industry may harm the environment. However, users of so called "waste products" (such as orange peels or eucalyptus leafs) have a low impact since the environment would also be harmed without using waste streams. | Data Source: Research |
| 100 | Waste recyclable | >Recycling of material is usually a valuable substitute of raw materials. The energy used to produce this waste is already included in the $CO_2$ parameter. | Data Source: Research |
| 100 | Waste re-usable as side stream | >If it is known that waste (e.g. NaCl in Chloralkali process) is recovered and used as a raw material, it is not longer considered as waste. | Data Source: Research |

Waste used as fuel or as fertilizer is considered as waste, because most of the Symrise fragrance raw materials are categorized this way and therefore it's not a differentiator.

Handling of Data Gaps

Usually suppliers prefer to not share process parameter to protect their knowledge. For processing steps with high energy consumptions and material losses (e.g. crystallization and distillation) standard factors related to own manufacturing data and Probas information are used.

Water Consumption and/or Pollution

The availability of water is dependent on water resources on one hand and water removal on the other. If water removal exceeds a certain percentage of resources, we speak of 'water stress'. 'Extreme water stress' applies when the removal exceeds 40% of the resources. The scoring is illustrated by the following Scheme 10.

Scheme 10: Scoring

STEP 1 Evaluation of the 'Water Score' of each reactant based on the following scoring system:

| Score | Criterion | Description | Data Source |
|---|---|---|---|
| 100 | Reactant is side product/results from waste streams | >If a substance is a side product from a resource (e.g. orange, wood) that is cultivated for other purposes in the first place, a score of 100 applies. Primary products, such as orange juice or wood for the furniture industry may harm the environment. However, users of so called "waste products" (such as orange peels or eucalyptus leafs) have a low impact since the environment would also be harmed without using waste streams. | Data Source: Research |
| 100 | Reactant results from chemicals synthesis/ product with very low water consumption | >If a substance results from chemical synthesis, a score of 100 applies. Agricultural chemical processes are usually not that water demanding | Data Source: Research |
| 100 | Global bulk products → Production volume of >1.000 t/annum | For big bulk products which are produced in more than 1.000 t/annum a score of 100 applies since products derived in high tonnages are considered as less critical. A detailed list can be found here: Basic Chemicals and Production and here http://echa.europa.eu/de/ 1000 t is the threshold value of REACH. Experience has shown that large producers have a high degree of automatization ensuring advanced process control due to REACH requirements and cost pressure. Small suppliers are not as well-positioned. Also due to high automatization, water use is comparably low (approx. 1 $m^3$/t). | Data Source: List of Basic Chemicals and Production Volumes (Appendix) |
| 100 | Sourcing from non-stressed areas | >If a process shows high water consumption, it needs to be checked if water is sourced from so called "water stressed" areas to evaluate the materiality correctly. To identify such risk, the following water tool is used: http://www.wri.org/resources/charts-graphs/water-stress-country A rating of 3 to 5 is considered as "water stress". | Data Source: Research/Link |
| 075 | Sourcing from water stressed area-very low consumption (<0.1 $m^3$/kg) | >e.g. Vetiver (regulates groundwater) Source: http://www.vetiver.com/THN_vetiver_water.pdf | Data Source: Research/Link |
| 050 | Sourcing from water stressed area-low consumption (<=1 $m^3$/kg) | >e.g. Citrus fruits, pulses, roots, tubers, corn, sugarcane Source: http://www.lenntech.com/water-food-agriculture.htm | Data Source: Research/Link |
| 025 | Sourcing from water-stressed area medium consumption (>=1 $m^3$/kg && <10 $m^3$/kg) | >e.g. Palm oil, Rice, Wheat, Wood Source: ttp://www.sert.nu.ac.th/IIRE/FP_V6N1%281%29.pdf and http://www.lenntech.com/water-food-agriculture.htm | Data Source: Research/Link |
| 000 | Sourcing from water-stressed area high consumption >=10 m3/kg) | >e.g. Peppermint, Patchouli Source: http://www.downtoearth.org.in/news/farmers-quit-mentha-32914 | Data Source: Research/Link |
| 000 | No data available | >If no data is available, a score of 0 applies | Data Source: / |

STEP 2 Calculation of the 'Water Score' of composed products. Each reactant counts into the product result related to molar masses used:

$$\frac{\left(\begin{array}{l}\text{'Reactant } A \text{ Molar Mass'} * \text{'Reactant } A \text{ Water'} + \\ \text{'Reactant } B \text{ Molar Mass'} * \text{'Reactant } B \text{ Water ...'}\end{array}\right)}{\text{'('Reactant } A \text{ Molar Mass'} + \text{'Reactant } B \text{ Molar Mass')}} = \text{Water Score}$$

SUMMARY

The following chapter shall provide a brief overview how the parameters explained above are calculated. As explained above a lot of indicators and values (such as for example biodegradability or carbon dioxide emissions) can be taken from public data bases. In case not indicated otherwise numbers shall be taken as percent.

The score for biodegradability of the compound or the compounds is evaluated according to OECD Method 301/302 or equivalent.

The score for the overall ecological toxicity S(ETOX) is calculated according to the following equation (3):

$$S(ETOX) = \tfrac{2}{3} * MAX(Ma; Pa) + \tfrac{1}{3} * ((Mb*Cb) + \ldots (Mz*Cz)) \quad (3)$$

wherein P stands for the Product Eco Tox Score and S stands for Supplier Performance Score on condition that the formulation contains a to z compounds.

The score for the overall human toxicity S(HTOX) is calculated according to the following equation (4):

$$S(HTOX) = \tfrac{2}{3} * MAX(Ma; Pa) + \tfrac{1}{3} * (Mb*Cb) + \ldots (Mz*Cz) \quad (4)$$

wherein P stands for the Product Human Tox Score and S stands for Supplier Performance Score on condition that the formulation contains a to z compounds.

The score for the overall land use S(LU) is calculated according to the following equation (5):

$$S(LU) = \frac{(M_a * D_a) + (M_b * D_b) + (M_c * D_c) + \ldots (M_z * D_z)}{M_a + M_b + M_c + \ldots M_z} \quad (5)$$

wherein M stands for the molar mass of a specific compound and D stands for its Land Use on condition that the formulation contains a to z compounds.

The score for the overall renewability S(REN) is calculated according to the following equation (6):

$$S(REN) = \frac{(M_a * D_a) + (M_b * D_b) + (M_c * D_c) + \ldots (M_z * D_z)}{R_a} \quad (6)$$

wherein M stands for the count of C atoms of a specific compound, D stands for its Renewability and P stands for C atoms of product of the synthesis on condition that the formulation contains a to z compounds.

The score for the overall traceability S(TRA) is calculated according to the following equation (7):

$$S(TRA) = \frac{(M_a * D_a) + (M_b * D_b) + (M_c * D_c) + \ldots (M_z * D_z)}{M_a + M_b + M_c + \ldots M_z} \quad (7)$$

wherein M stands for the molar mass of a specific compound and D stands for its Traceability on condition that the formulation contains a to z compounds.

The score for the overall waste generation S(WAS) is calculated according to the following equation (8):

$$A1 = \frac{(M_a * C_a) + (M_b * C_b) + (M_c * C_c) + \ldots (M_z * C_z)}{P_a} \quad (8a)$$

$$A2 = \frac{(M_a + M_b + M_c + \ldots M_z) - P_a}{P_a} \quad (8b)$$

$$B = (A1 + A2) * \frac{(100 + L)}{100} \quad (8c)$$

$$S(WAS) = (10 - B) * 10 \quad (8d)$$

wherein:
M stands for the molar mass of a specific compound and
C stands for its e-Factor
on condition that the formulation contains a to z compounds
P stands for molar mass of product of the synthesis
A1 means the reactant based e-factor
A2 means the loss of molar mass during synthesis
L stands for the losses of compounds during processing
B represents the overall e-factor.

The score for the overall water consumption S(WAT) is calculated according to the following equation (9):

$$S(WAT) = \frac{(M_a * D_a) + (M_b * D_b) + (M_c * D_c) + \ldots (M_z * D_z)}{M_a + M_b + M_c + \ldots M_z} \quad (9)$$

wherein M stands for the molar mass of a specific compound and D stands for its Traceability on condition that the formulation contains a to z compounds.

In the following the present invention is illustrated by working examples without limiting the invention to them.

EXAMPLES

Method Description
Fragrance Raw Material Scoring
(I) For each fragrance raw material, a product sheet is set up in a tailor-made IT system
  (a) Evaluation of synthesis route: The common synthesis route of each raw material is identified by a senior chemist with advanced knowledge of the Symrise raw material portfolio and material flows
    Handling of data gaps. The main challenge of the scorecard evaluation is to identify the most common route of synthesis due to lack of information from suppliers. For some ingredients, well-known and robust processes are established which can be found in the literature or patents. However, in some cases there are several possibilities to produce the same chemical depending on availability of raw materials and/or technologies available on site. It is assumed that the environmental impact between several possibilities is not that high, because raw material costs on the global spot market are usually comparable and therefore environmental costs and resource consumption should also be on a similar level.
  (b) Collection of data: Raw material information including sustainability data are collected:
    (b1) Suppliers are ask to deliver data to clarify uncertainties, e.g. renewable source, palm oil derivatives
    (b2) Public databases like Probas, Gestis or REACH are reviewed for relevant data
    (b3) If no relevant data is available, desk research is conducted. Studies and literature are used as reference.
    (b4) Data gaps are filled with generic data from defined sources (see reference in each parameter)
    The overall data is consolidated in one table which is exportable to Excel
  (c) Definition of ID: The raw material data is assigned to Symrise product codes for further processing
(II) For each ingredient/reactant a product sheet is maintained.
(III) The fragrance raw materials are evaluated according to all 10 scorecard criteria. The fragrance raw material score is calculated automatically based on the synthesis route and all collected data.
(IV) Analysis and comparison: The objective of the product sustainability scorecard is to increase transparency and knowledge about raw material used for fragrance composition. Different raw materials can be compared according to their scores.

Figures 2A, 2B:
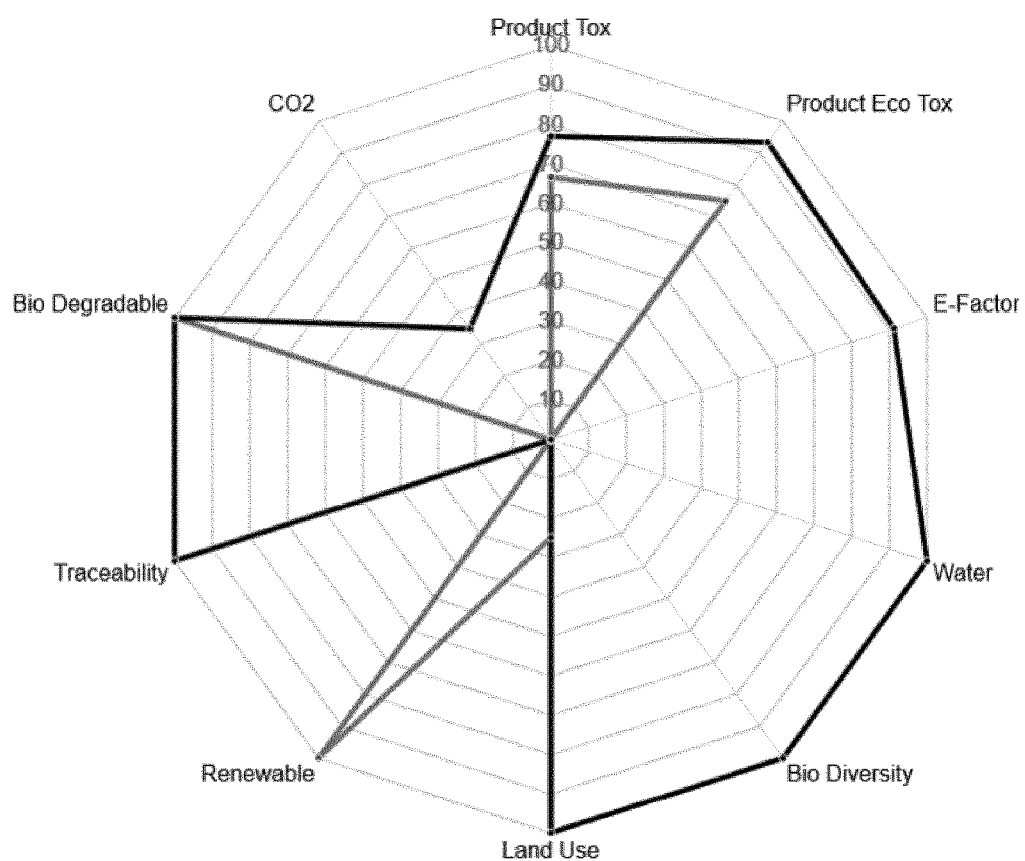

Product Scoring
(I) The recipe/fragrance formula of a Symrise product is set up
(II) Based on a recipe/fragrance formula, a product score is calculated automatically by consolidating all involved fragrance raw material scores The results are consolidated as shown in FIG. 2a and can be exported as radar diagram as shown in FIG. 2b.

The user will receive information about the ratio covered as depicted in Table 5.

TABLE 5

User information

| Calculation | Figure | Information |
|---|---|---|
| Quantity | 26.288 | Total production volume in kg |
| Quantity covered | 22.006 | Share of total volume that is covered by scoring methodology in kg |
| Ratio covered | 83.4% | Minimum of 80% is exceeded |
| Result/Quality | 67.6 | Final product score |

Figure 3:
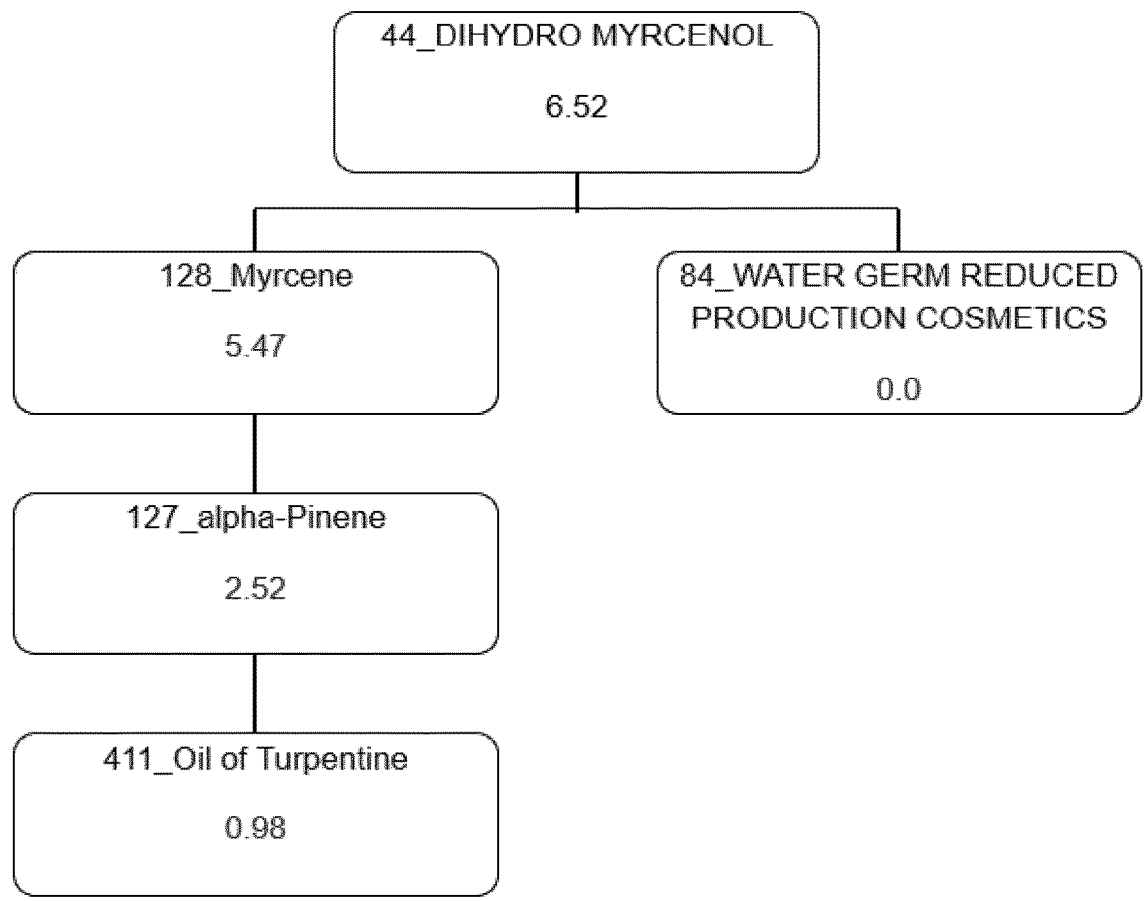
FIG. 3 schematically illustrates how a route cause analysis for each scorecard criteria can be conducted via an automatic analysis tool in each product sheet directly.

A route cause analysis for each scorecard criteria can be conducted via an automatic analysis tool in each product sheet directly as shown in FIG. 3.

Example 1

Figure 4:
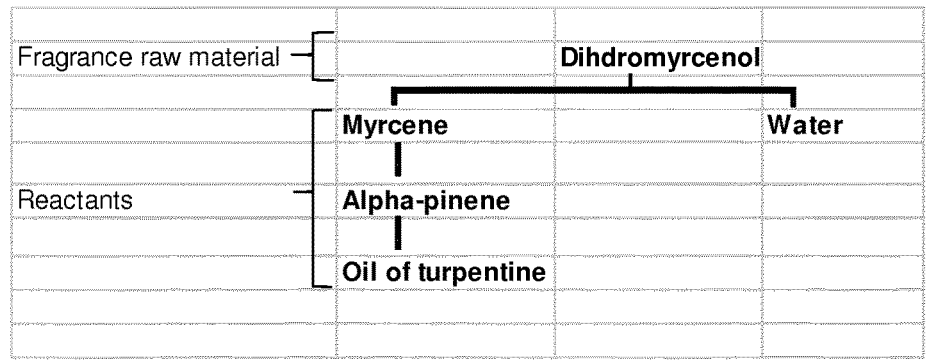
FIG. 4 schematically illustrates how as a first step the synthesis route of 44DHM is evaluated and information concerning the raw materials including sustainability data (e.g. molar mass, processing, C-atoms, GHS hazard statements etc.) are collected.
Figure 5A:
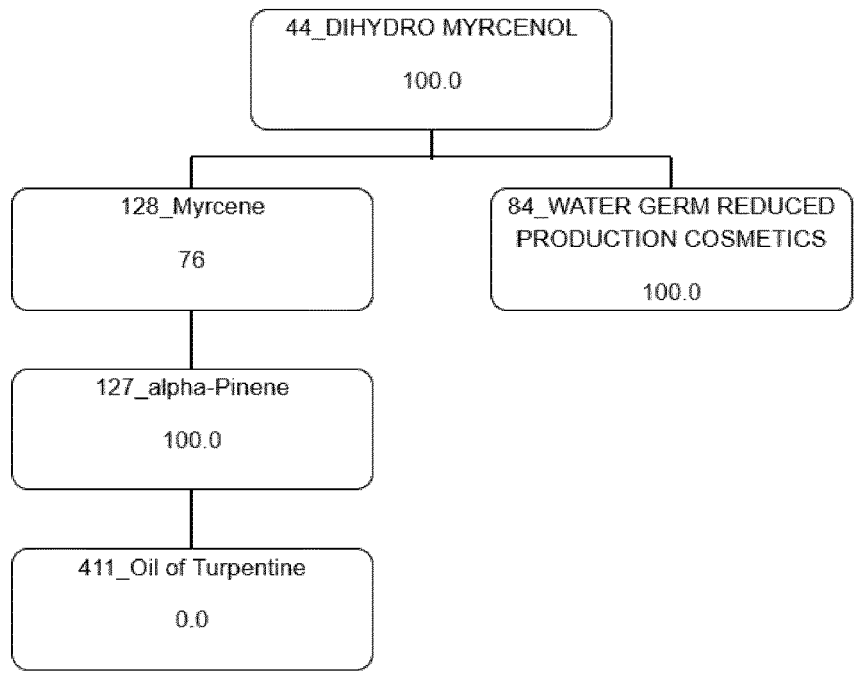
FIGS. 5A-5J each schematically illustrate the details of the evaluation.
Figure 5B:
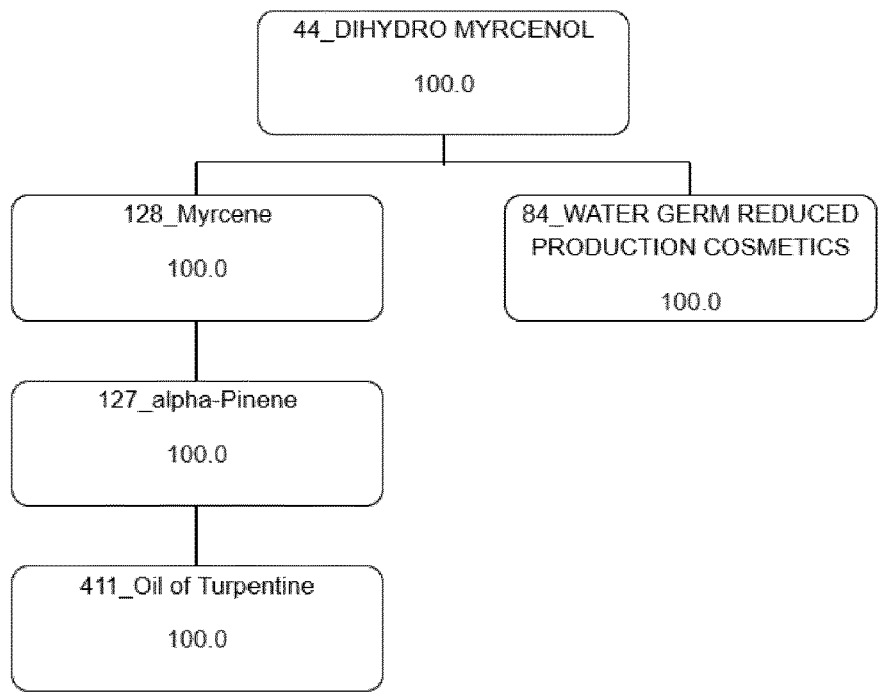
Figure 5C:
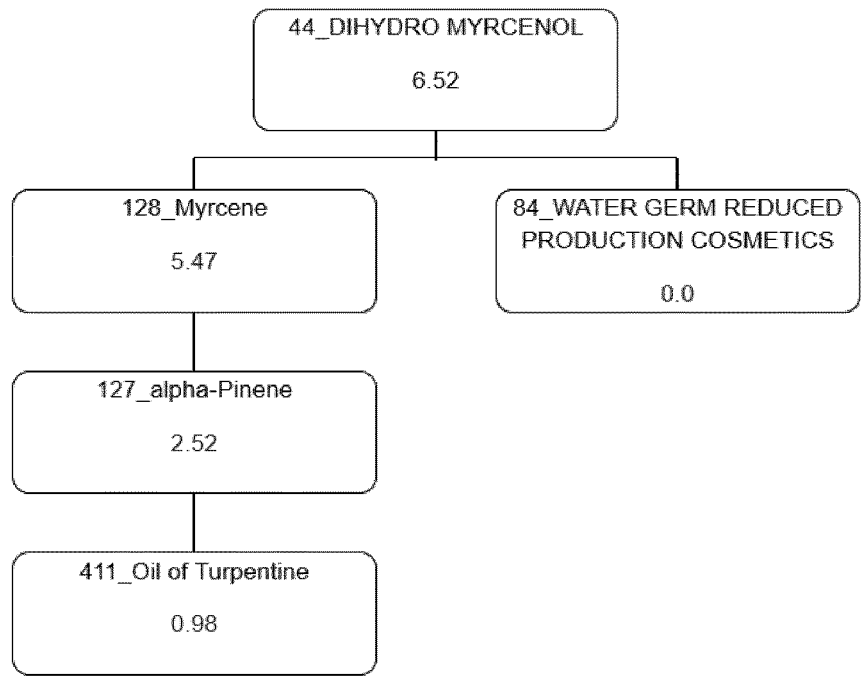
Figure 5D:
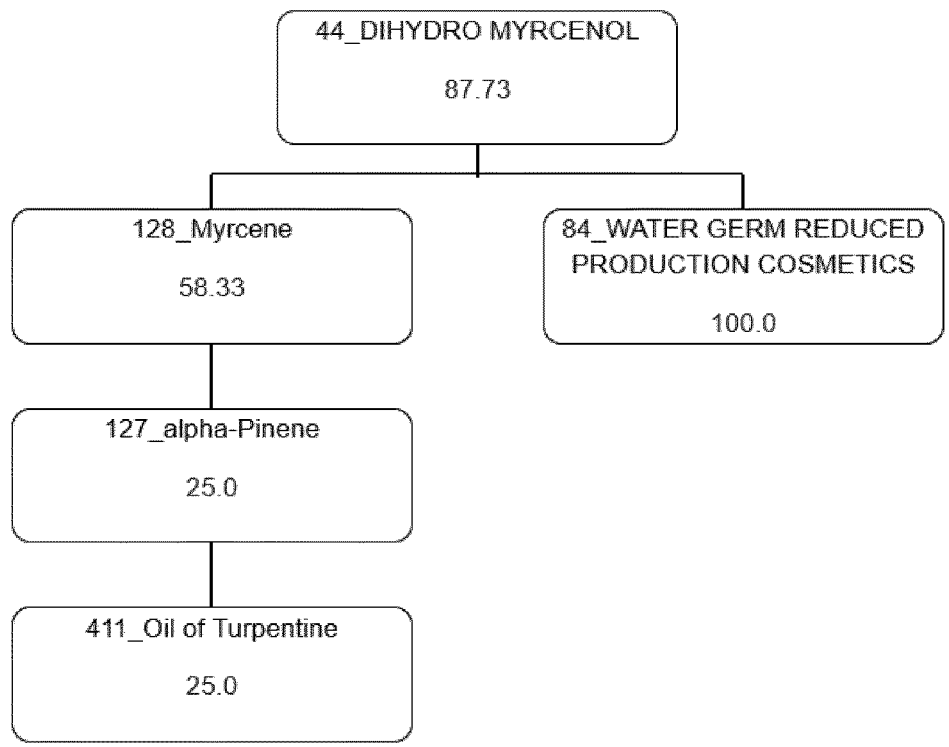
Figure 5E:
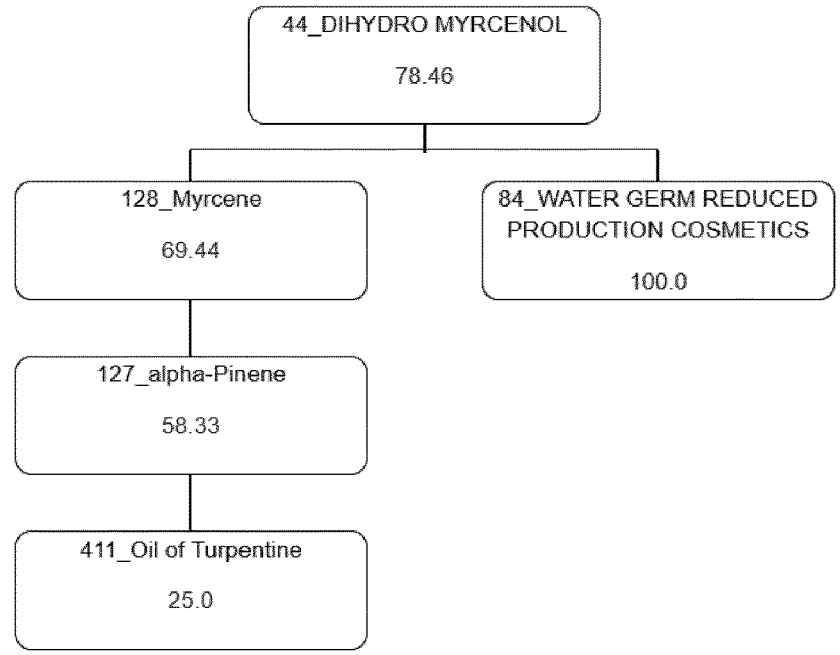
Figure 5F:
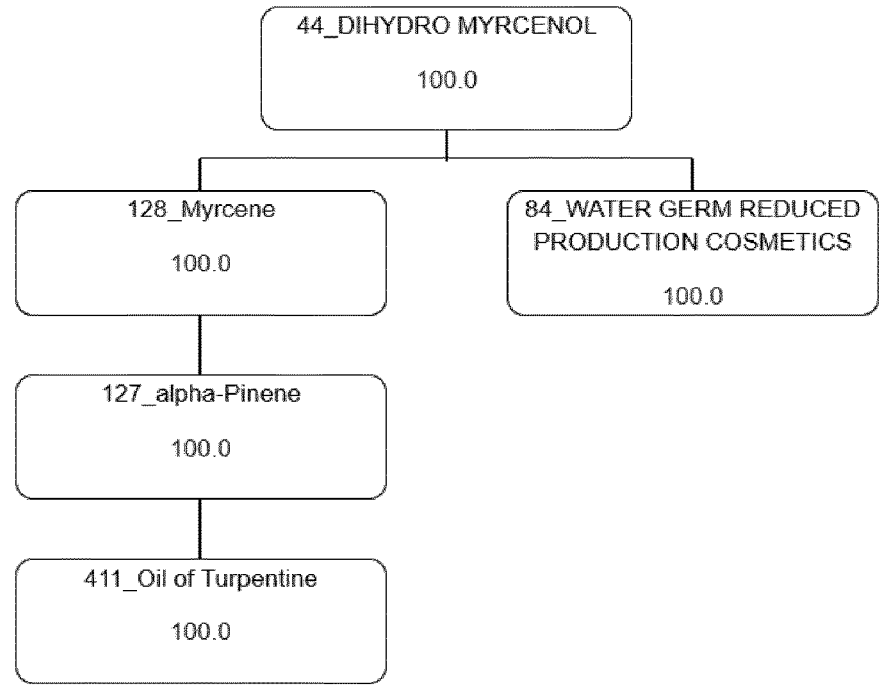
Figure 5G:
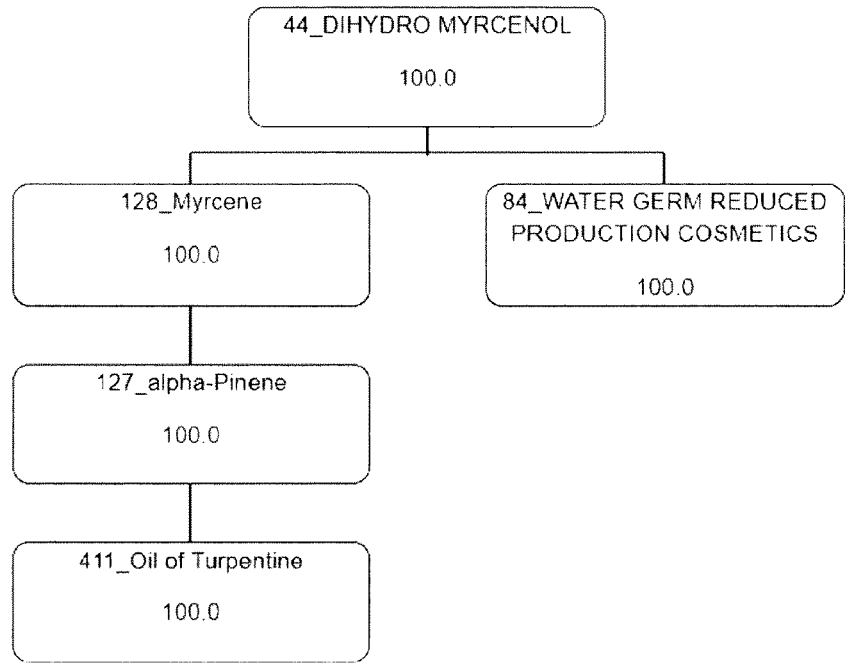
Figure 5H:
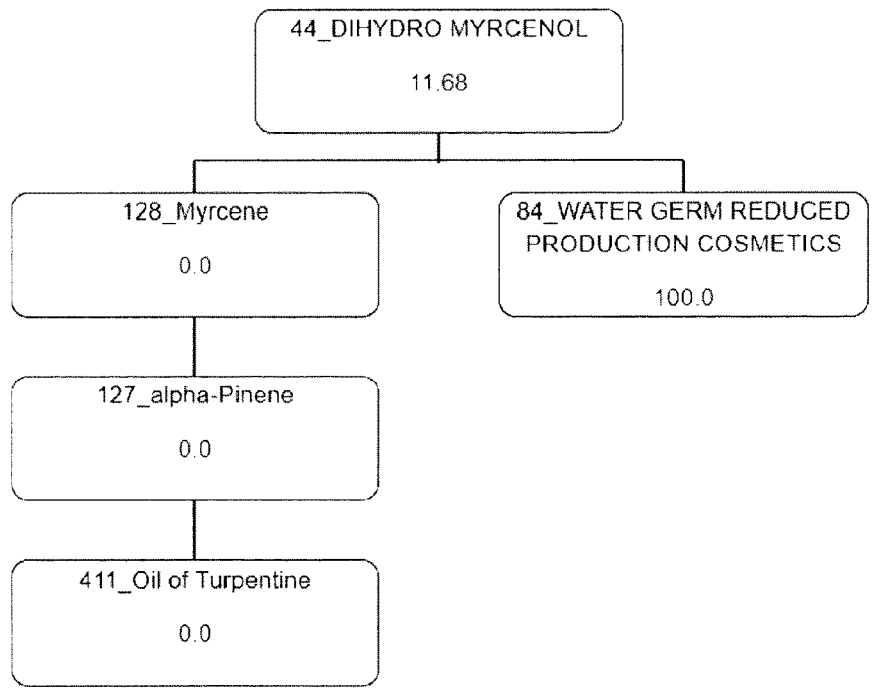
Figure 5I:
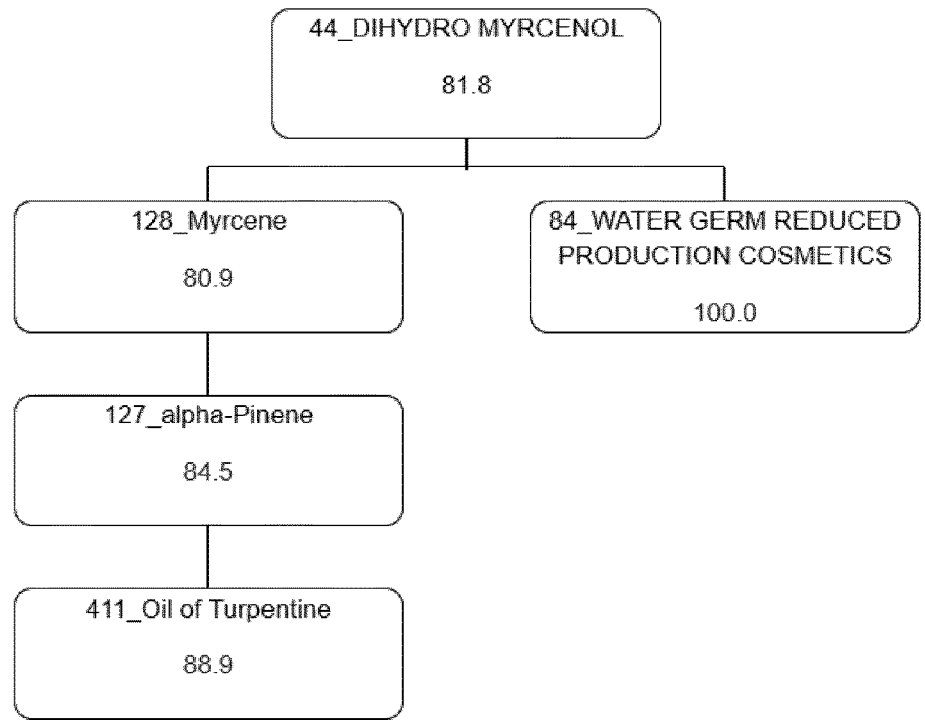
Figure 5J:
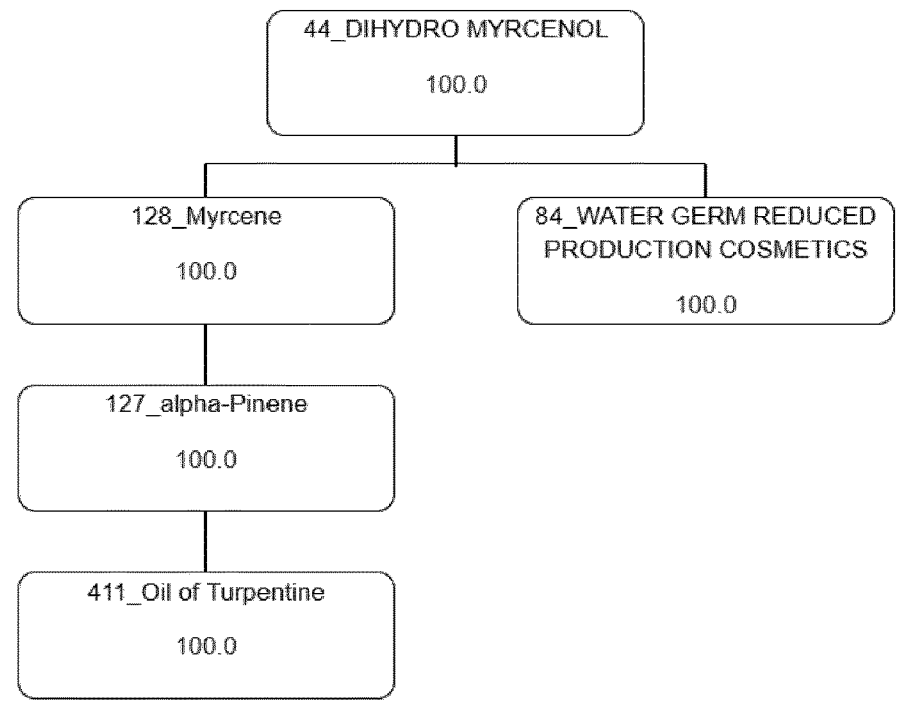
Figure 7:
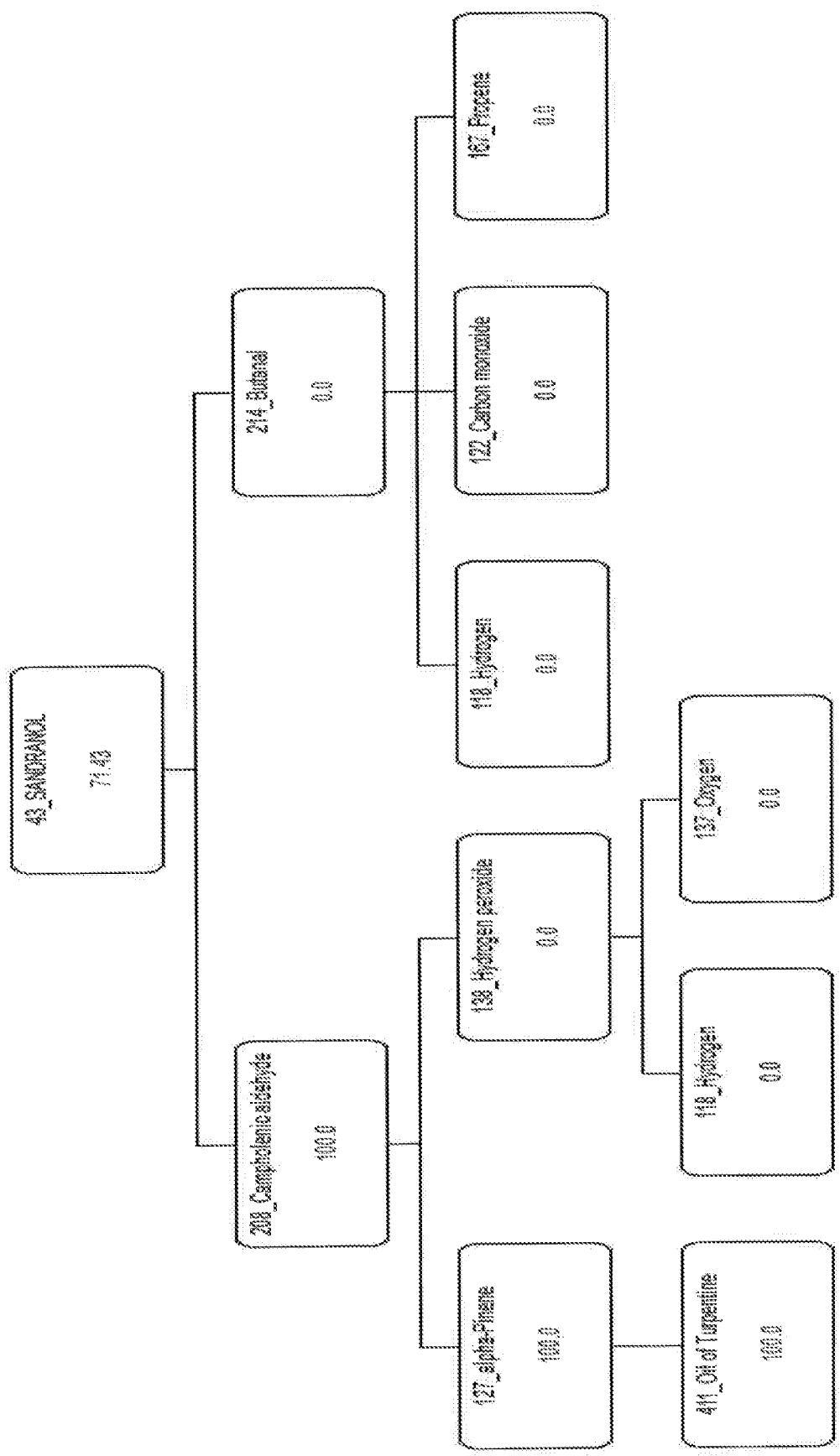
FIG. 7 shows as an example the renewability score of sandranol.

44_Dihydro Myrcenol (44DHM)
As a first step the synthesis route of 44DHM is evaluated (FIG. 4) and information concerning the raw materials including sustainability data (e.g. molar mass, processing, C-atoms, GHS hazard statements etc.) are collected. In the present example 44DHM was used in a composition comprising also dipropylene glycol (DPG) and alpha-hexyl cinnamic aldehyde (HCA). For each component a product data sheet was prepared.
44DHM was evaluated according to all 10 scorecard criteria. The score was calculated automatically based on the data inserted. Finally, the overall data was consolidated. The results are shown in Table 6:

TABLE 6

Consolidated score of 44DHM

| Parameter | Result |
|---|---|
| Carbon dioxide | 34.8 |
| Renewability | 100.0 |
| Product Tox | 80.38 |
| Product EcoTox | 87.73 |
| E-Factor | 92.90 |
| Water | 100.00 |
| Biodiversity | 100.00 |
| Land use | 100.00 |
| Traceability | 11.68 |
| Biodegradability | 100.00 |
| RESULT (AVERAGE) | 80.7 |

The details of the evaluation are shown in FIGS. 5A to 5J. The recipe/fragrance formula consisting of 44DHM, DPG and HCA was set up as depicted in FIG. 6; all scores were above 70. The total score for the formulation resulted to 82.2

The invention claimed is:

1. A method for identifying fragrance compounds with low environmental impact and high degree of sustainability encompassing the following steps:
   (a) providing a fragrance compound or a fragrance composition of interest;
   (b) measuring performance of the fragrance compound or fragrance composition for each of the following parameters followed by normalizing to a scale from 0 to 100 without dimension to identify fragrance compounds with low environmental impact and high degree of sustainability, based on calculating scores for each of the following parameters:
      (b1) biodegradability;
      (b2) biodiversity;
      (b3) carbon dioxide emission;
      (b4) process safety with regard to ecological toxicity;
      (b5) process safety with regard to human toxicity;
      (b6) land use;
      (b7) renewability;
      (b8) traceability;
      (b9) waste generation; and
      (b10) water consumption and/or pollution,
   (c) summing up all scores and calculating the average product sustainability score (PSC); and
   (d) proceeding with those candidates showing a PSC of at least 70, wherein
   (i) the score for biodegradability of the compound or the composition is calculated according to OECD Method 301/302;
   (ii) the score for the overall biodiversity S(BIO) is calculated according to the following equation (1):

$$S(BIO) = \frac{(M_a * D_a) + M_b * D_b) + (M_c * D_c) + \ldots (M_z * D_z)}{M_a + M_b + M_c + \ldots M_z} \quad (1)$$

wherein M stands for the molar mass of a specific compound and D stands for its biodiversity on condition that the formulation contains a to z compounds;
   (iii) the score for the overall carbon dioxide impact S($CO_2$) is calculated according to following equation (2):

$$A1 = \frac{(M_a * C_a) + M_b * C_b) + (M_c * C_c) + \ldots (M_z * C_z)}{P_a} \quad (2a)$$

$$B = \frac{(A1 + F) * (100 + L)}{100} \quad (2b)$$

$$S(CO2) = (10 - B) * 10 \quad (2c)$$

wherein M stands for the molar mass of a specific compound and C stands for its carbon dioxide emission on condition that the formulation contains a to z compounds, F stands for processing related carbon dioxide emission, A1 means the reactant based carbon dioxide emission, L stands for the losses of compounds during processing, and B represents the overall carbon dioxide emissions;
   (iv) the score for the overall ecological toxicity S(ETOX) is calculated according to the following equation (3):

$$S(ETOX) = \tfrac{2}{3} * MAX(Ma;Pa) + \tfrac{1}{3} * ((Mb*Cb) + \ldots (Mz*Cz)) \quad (3)$$

wherein P stands for the Product Eco Tox Score and S stands for Supplier Performance Score on condition that the formulation contains a to z compounds;
   (v) the score for the overall human toxicity S(HTOX) is calculated according to the following equation (4):

$$S(HTOX) = \tfrac{2}{3} * MAX(Ma;Pa) + \tfrac{1}{3} * (Mb*Cb) + \ldots (Mz*Cz) \quad (4)$$

wherein P stands for the Product Human Tox Score and S stands for Supplier Performance Score on condition that the formulation contains a to z compounds;
   (vi) the score for the overall land use S(LU) is calculated according to the following equation (5):

$$S(LU) = \frac{(M_a * D_a) + M_b * D_b) + (M_c * D_c) + \ldots (M_z * D_z)}{M_a + M_b + M_c + \ldots M_z} \quad (5)$$

wherein M stands for the molar mass of a specific compound and D stands for its Land Use on condition that the formulation contains a to z compounds;

(vii) the score for the overall renewability S(REN) is calculated according to the following equation (6):

$$S(REN) = \frac{(M_a * D_a) + M_b * D_b) + (M_c * D_c) + \ldots (M_z * D_z)}{R_a} \quad (6)$$

wherein M stands for the count of C atoms of a specific compound and D stands for its Renewability; P stands for C atoms of product of the synthesis on condition that the formulation contains a to z compounds;

(viii) the score for the overall traceability S(TRA) is calculated according to the following equation (7):

$$S(TRA) = \frac{(M_a * D_a) + M_b * D_b) + (M_c * D_c) + \ldots (M_z * D_z)}{M_a + M_b + M_c + \ldots M_z} \quad (7)$$

wherein M stands for the molar mass of a specific compound and D stands for its Traceability on condition that the formulation contains a to z compounds;

(ix) the score for the overall waste generation S(WAS) is calculated according to the following equation (8):

$$A1 = \frac{(M_a * C_a) + M_b * C_b) + (M_c * C_c) + \ldots (M_z * C_z)}{P_a} \quad (8a)$$

$$A2 = \frac{(M_a + M_b + M_c + \ldots M_z) - P_a}{P_a} \quad (8b)$$

$$B = (A1 + A2) * \frac{(100 + L)}{100} \quad (8c)$$

$$S(WAS) = (10 - B) * 10 \quad (8d)$$

wherein M stands for the molar mass of a specific compound and C stands for its e-Factor on condition that the formulation contains a to z compounds, P stands for molar mass of product of the synthesis, A1 means the reactant based e-factor, A2 means the loss of molar mass during synthesis, L stands for the losses of compounds during processing, and B represents the overall e-factor;

(x) the score for the overall water consumption S(WAT) is calculated according to the following equation (9):

$$S(WAT) = \frac{(M_a * D_a) + M_b * D_b) + (M_c * D_c) + \ldots (M_z * D_z)}{M_a + M_b + M_c + \ldots M_z} \quad (9)$$

wherein M stands for the molar mass of a specific compound and D stands for its Traceability on condition that the formulation contains a to z compounds.

\* \* \* \* \*